United States Patent
Bouras et al.

(10) Patent No.: US 12,378,515 B2
(45) Date of Patent: *Aug. 5, 2025

(54) METHOD FOR CLEANING A REACTOR FOR PROCESSING A LIGNOCELLULOSIC BIOMASS

(71) Applicants: IFP Energies nouvelles, Rueil-Malmaison (FR); INSTITUT NATIONAL DE RECHERCHE POUR L'AGRICULTURE, L'ALIMENTATION ET L'ENVIRONNEMENT, Paris (FR); AGRO INDUSTRIES RECHERCHE ET DEVELOPPEMENT, Pomacle (FR)

(72) Inventors: Meriem Bouras, Rueil-Malmaison (FR); Caroline Aymard, Rueil-Malmaison (FR); Olivier Carnnot, Baccones (FR)

(73) Assignees: IFP Energies nouvelles, Rueil-Malmaison (FR); INSTITUT NATIONAL DE RECHERCHE POUR L'AGRICULTURE, L'ALIMENTATION ET L'ENVIRONNEMENT, Paris (FR); AGRO INDUSTRIES RECHERCHE ET DEVELOPPEMENT, Pomacle (FR)

( * ) Notice: Subject to any disclaimer, the term of this patent is extended or adjusted under 35 U.S.C. 154(b) by 1034 days.

This patent is subject to a terminal disclaimer.

(21) Appl. No.: 17/416,213

(22) PCT Filed: Dec. 13, 2019

(86) PCT No.: PCT/EP2019/085107
§ 371 (c)(1),
(2) Date: Jun. 18, 2021

(87) PCT Pub. No.: WO2020/126916
PCT Pub. Date: Jun. 25, 2020

(65) Prior Publication Data
US 2022/0056395 A1     Feb. 24, 2022

(30) Foreign Application Priority Data
Dec. 21, 2018   (FR) ...................... 1873757

(51) Int. Cl.
*C12M 1/00*         (2006.01)
*B08B 9/08*         (2006.01)
*C12P 7/10*         (2006.01)
*C12P 19/14*        (2006.01)

(52) U.S. Cl.
CPC ........... *C12M 39/00* (2013.01); *B08B 9/08* (2013.01); *C12M 21/12* (2013.01); *C12M 23/58* (2013.01); *C12P 7/10* (2013.01); *C12P 19/14* (2013.01); *B08B 2209/08* (2013.01); *B08B 2230/01* (2013.01); *C12P 2201/00* (2013.01); *C12P 2203/00* (2013.01)

(58) Field of Classification Search
None
See application file for complete search history.

(56) References Cited

U.S. PATENT DOCUMENTS

2010/0330633 A1\* 12/2010 Walther ................. C12M 45/06
                                              435/150
2013/0236941 A1   9/2013 Burns-Guydish et al.
2017/0314046 A1\* 11/2017 Nilsen ................... C02F 11/185
2019/0241984 A1   8/2019 Hudebine et al.

FOREIGN PATENT DOCUMENTS

WO         18015227 A1     1/2018

OTHER PUBLICATIONS

Rickard Fornell. "Technical description of the Biorefinery Demonstration plant in Ornskoldsvik" Aug. 8, 2014 (Aug. 8, 2014). pp. 1-6.
Anneli Petersson. "Description of system for cultivation and fermentation in the Biorefinery Demo Plant in Ornskoldsvik" Aug. 8, 2014 (Aug. 8, 2014). pp. 1-2.
Yusuf Cristi et al. "Clean-in-place systems for industrial bioreactors: Design. validation and operation" Journal for Industrial Microbiology, UK, vol. 13, No. 4, Jul. 1, 1994 (Jul. 1, 1994), pp. 201-207 DOI: 10.1007/BF01569748 ISSN: 0169-4146, XP055633871.
Bill Miley et al. "Large-Scale Fermentation Systems: Hygienic Design Principles" Chemical Engineering. Engineering Practice, Nov. 1, 2015 (Nov. 1, 2015), pp. 59-65.
Dirk Hebel. "Making Glass Bioreactors CIP and SIP Capable" Genetic Engineering & Biotechnological News, vol. 34, No. 16, Jan. 1, 2014 (Jan. 1, 2014), pp. 1-4.
David J. Walker et al. "Process Optimization of Steam Explosion Parameters on Multiple Lignocellulosic Biomass Using Taguchi Method—A Critical Appraisal" Frontiers in Energy Research, vol. 6, Jun. 1, 2018 (Jun. 1, 2018), pp. 1-13 DOI: 10.3389/fenrg.2018.00046.
International Search Report PCT/EP2019/085107 dated Mar. 25, 2020 (pp. 1-3).

\* cited by examiner

*Primary Examiner* — Christian L Fronda (57) ABSTRACT

The present invention concerns a method for cleaning a reactor (4) for treating a lignocellulosic biomass (P), said method comprising the following steps:
a) draining the reactor of the reaction mixture containing the biomass,
b) filling the reactor with a basic aqueous solution (EB),
c) draining the reactor,
d) injecting steam (V) into the reactor,
e) filling the reactor with an aqueous solution (E),
f) draining the reactor.

14 Claims, 4 Drawing Sheets

METHOD FOR CLEANING A REACTOR FOR PROCESSING A LIGNOCELLULOSIC BIOMASS

TECHNICAL FIELD

The invention relates to a method for treating lignocellulosic biomass to produce "second-generation" (2G) sugary liquors. These sugary liquors may be used to produce other products via a biochemical pathway (e.g., alcohols such as ethanol, butanol or other molecules, or solvents such as acetone, etc.). This method comprises various steps, including generally the three steps of liquor preparation, impregnation of the biomass with this liquor, and pretreatment of the impregnated biomass by cooking, in particular with steam explosion.

PRIOR ART

Lignocellulosic biomass represents one of the most abundant renewable resources on Earth. The substrates considered are very varied, they relate both to ligneous substrates such as various woods (hardwoods and softwoods), coproducts derived from agriculture (wheat straw, corn cobs, etc.) or from other agrifood, paper, etc. industries.

The method for the biochemical conversion of the lignocellulosic material into 2G sugary liquors notably comprises a pretreatment step and a step of enzymatic hydrolysis with an enzymatic cocktail. These methods also usually include an impregnation step before the pretreatment. The sugary liquors resulting from the hydrolysis are then treated, for example by fermentation, and the method also comprises separation steps and/or a step of purifying the end product.

Lignocellulosic biomass is composed of three main polymers: cellulose (35 to 50%), which is a polysaccharide essentially consisting of hexoses; hemicellulose (20 to 30%), which is a polysaccharide essentially consisting of pentoses; and lignin (15 to 25%), which is a polymer of complex structure and of high molecular weight, composed of aromatic alcohols connected via ether bonds. These various molecules are responsible for the intrinsic properties of the plant wall and are organized in a complex entanglement.

Among the three base polymers that make up lignocellulosic biomass, cellulose and hemicellulose are the ones that enable the production of 2G sugary liquors.

Usually, hemicellulose is predominantly broken down into monomeric and oligomeric sugars during the pretreatment, and cellulose is converted into glucose by enzymatic hydrolysis. However, access to the raw cellulose in the native substrate remains difficult for enzymes to access, hence the need for a pretreatment. This pretreatment makes it possible to modify the physicochemical properties of the lignocellulosic material in order to improve the accessibility of the cellulose to enzymes and its reactivity to enzymatic hydrolysis.

Numerous technologies of interest to the invention for carrying out this pretreatment exist, and will be referred to collectively hereinafter using the generic term "cooking", which involves heating the biomass at high temperature for a defined duration. Known techniques include, in particular, acid cooking, where the biomass is contacted with an acidic solution before/during cooking, and alkaline cooking, where the biomass is contacted with a basic solution before/during cooking. Another known technique is cooking (acid, alkaline or without impregnation) by steam explosion, where the biomass is subjected to pressurized steam.

There are also pretreatment methods known as "organosolv pulping". The latter method involves pretreatment in the presence of one or more organic solvents and generally water. The solvent may be an alcohol (ethanol), an acid such as acetic acid or formic acid, or else acetone, or alternatively a mixture of these compounds. "Organosolv pulping" methods lead to at least partial dissolution of the lignin and partial dissolution of the hemicelluloses. There are thus two outlet streams: the pretreated substrate with residual cellulose, hemicellulose and lignin, and the solvent phase which contains the dissolved lignin and a portion of the hemicelluloses. There is generally a step of regeneration of the solvent, which makes it possible to extract a lignin stream. Certain "organosolv pulping" treatments (notably with ethanol) may be coupled with the addition of a strong acid (such as $H_2SO_4$). It is also possible to contemplate contacting the biomass with the solvent via an impregnation reactor before the cooking phase or contacting the biomass with the acidic catalyst before performing cooking by "organosolv pulping".

Various configurations are reported, for example, in the document "Production of bioethanol from lignocellulosic materials via the biochemical pathway: A review", M. Balat, Energy Conversion and Management 52 (2011) 858-875, or else in the document "Bioethanol production from agricultural wastes: an overview", N. Sarkar, S. Kumar Ghosh, S. Bannerjee, K. Aikat, Renewable Energy 37 (2012) 19-27.

One of the most effective pretreatments is the aforementioned steam explosion cooking, as it enables almost complete hydrolysis of hemicellulose and a significant improvement in the accessibility and reactivity of cellulose with respect to enzymes. This pretreatment may be preceded/followed by one or more other treatments, and it is this which will be of more particular interest to the invention—which is not limited thereto in its application, however. It has been shown that the pretreatment reactors, especially cooking reactors, had a propensity to fouling—heating the reaction mixture in the reactor at high temperature leads to the production of various solid residues, which stick to the inside walls of the reactor. These residues progressively accumulate over a time longer than the average residence time of the biomass in the reactor. They may gradually give rise to operational problems, such as, for example, a risk of plugging of the reactor outlet, increased difficulty in conveying the biomass within the reactor, and, generally, their presence negatively impacts the performance characteristics of the reactor.

A first solution provided to suppress these residues involves draining the reactor, thus stopping it, and opening it, to perform cleaning of the inside walls of the reactor by mechanical and/or hydraulic action, in other words by scraping the walls and/or by applying water pressurized to several hundred bar. While this procedure is effective, it does consume time and energy, it necessarily involves not only stopping the reactor but also waiting for it to cool (cooking takes place at a temperature of greater than 100° C. and under pressure), then opening it, performing cleaning, reclosing the reactor and bringing it back to temperature, before restarting production.

The aim of the invention is consequently to overcome these disadvantages. More specifically, the invention aims to develop a method for removing some or all of these residues that is effective while reducing reactor downtime and the expenditures of energy employed in implementing the method.

SUMMARY OF THE INVENTION

A first subject of the invention is a method for cleaning a reactor for treating a lignocellulosic biomass, said method comprising the following steps:
- a) draining the reactor of the reaction mixture containing the biomass,
- b) filling the reactor with a basic aqueous solution,
- c) draining the reactor,
- d) injecting steam into the reactor,
- e) filling the reactor with an aqueous solution,
- f) draining the reactor.

"Treatment" in the context of the invention refers to any step aiming to modify one or more characteristics of the biomass. This may in particular be a pretreatment, a term known in the field of lignocellulosic biomass treatment with the aim of preparing the biomass for enzymatic hydrolysis.

The basic solution used in step b) preferably has a pH before introduction into the reactor of at least 9, in particular at least 10, preferably at least 11 or 12.

The aqueous solution used in step e) preferably has a pH, before introduction into the reactor, which is substantially neutral, in particular a pH within a range of 6-8 or preferably 6.5-7.5, and advantageously is close to 7.

The invention has thus developed a method for cleaning the reactor in multiple steps that proves highly effective in suppressing all or virtually all the solid residue on the walls. The invention thus involves performing the cleaning in at least three phases: first a phase of treating the reactor, once drained, with a basic aqueous solution (which may also be referred to below by the term "basic liquor"), for example a solution containing KOH, followed by a steam treatment phase, and lastly a phase of rinsing with water.

This method is distinctly more simple to implement than mechanical or hydraulic cleaning: this is because it can be carried out with no need to open the reactor, as all that is needed is provision of the inlets/outlets for basic aqueous solution and for aqueous rinsing solution (or re-use of the inlets/outlets already present), and as the steam inlets are generally already present in the case of a reactor performing pretreatment by steam explosion cooking. Moreover, there is no need to wait for the reactor to cool to perform cleaning. It has even emerged, on the contrary, that carrying out all or part of the cleaning in a reactor which is still hot is highly favorable to the detachment of adhered residues. Since the reactor can remain relatively hot during cleaning, returning it to temperature on resumption of production may consume much less energy than with the previous mechanical/hydraulic solution.

Advantageously, the method according to the invention may optionally comprise at least one step a') of filling the reactor with an aqueous solution, followed by a step a") of draining the reactor, between step a) of draining the reaction mixture and step b) of filling with a basic aqueous solution. This aqueous solution is preferably at neutral pH or close to a neutral pH (between 6 and 8, preferably close to 7, like the aqueous solution used in step e), for example). It is therefore possible to add a rinsing phase before carrying out the treatment with the basic solution, which may prove beneficial when the biomass treatment takes place with a biomass impregnated with an acidic catalyst: as the invention has shown that the residues are removed and detach more easily in the presence of a basic solution, rinsing the reactor with water beforehand ensures that the basic solution will be fully effective, without at least a portion of the base being used to neutralize the traces of residual acidity in the reactor.

Advantageously, the method according to the invention may optionally further comprise, after step a), introducing particles of solid abrasive material into the reactor, either separately or by introducing the particles into the basic solution or into the or one of the aqueous solution(s). In that case the chemical action of the basic solution is supplemented by a mechanical action with abrasive particles, which will scrape/scratch the walls and facilitate detachment of the residues.

The basic aqueous solution and/or the or one of the aqueous solution(s) is or are preferably heated before introduction into the reactor, in particular to a temperature of at least 20° C., in particular of at least 60° C., and preferably at most 90° C.

The reason is that, as set out above, the efficacy of contacting the basic solution with the inside walls of the reactor is enhanced when this contacting is carried out hot. Similarly, the rinsing with water is also more effective when hot.

At least step b) of filling the reactor with the basic aqueous solution preferably takes place with the interior volume of the reactor at a temperature of at least 60° C., in particular of at least 80° C., in particular of at least 100° C. (and generally of at most 250 or 240 or 220° C.). As indicated above, contacting at high temperature conditions, markedly above the ambient temperature, facilitates the action of detaching the residues by the basic solution. It is then possible to benefit from the fact that the reactor generally performs the biomass pretreatment hot, by carrying out the cleaning while it is still hot (either by shutting off the reactor heating means, and employing the thermal inertia of the reactor, or by continuing to heat the reactor at its production temperature or at a temperature which, while lower, is greater than the ambient temperature.

Advantageously, during draining step c), the drained basic solution can be recovered for recycling, after optional filtration to remove the solid residues it may contain. It can be recycled, in whole or in part, for reinjection during the phase of contacting the inside walls of the reactor with the basic solution. It can also be retained for reinjection into the reactor during the subsequent cleaning operation. It can also be recycled, in whole or in part, by adding it to the aqueous solution or solutions used during steps a') and/or e).

A possibility is that, during draining step c), the basic solution drained is filtered for recovery of the solid residues it contains, and that these residues are treated, in particular by washing, for extraction of the basic solution from them for recycling thereof. The wash waters in question can be recycled by adding them as well to the basic solution: This further optimizes the consumption of basic solution in the cleaning according to the invention. These wash waters can also be added, in whole or in part, to the aqueous solutions used during steps a') and/or e).

The immersion of the reactor with the basic solution, when the reactor has been filled as per step b) and before it is drained, preferably has a duration of between 30 seconds and 4 days, in particular between 30 minutes and 10 hours, in particular between 1 and 3 hours. This duration is compatible with the requirements of industrial production, which can be modulated, according in particular to the frequency with which these cleaning operations are conducted.

The degree of filling of the reactor with the basic solution and/or with the or one of the aqueous solution(s) may be between 20 and 100%. This is because there is no need to fill the reactor completely with the solution—if, for example, the reactor is equipped with stirring means, or if it has been observed that the most significant residues tend to be at the base of the reactor. The term "degree of filling" is understood here to be the % of the total volume of the reactor, the total volume comprising the actual reaction volume, plus an upstream volume for the biomass inlet and a downstream volume for the biomass outlet.

The steam in step d) is preferably injected at a pressure of between $1.10^5$ and $20.10^5$ Pa, in particular between $12.10^5$ and $18.10^5$ Pa, in particular in the vicinity of $15.10^5$ Pa.

Steps e) and f) may be repeated at least twice, in particular between 2 and 10 times, with the repetition of these water rinses ensuring that all the residues which have detached from the walls are indeed extracted from the reactor; this also allows the removal from the reactor of the residual traces of basicity, which may be useful when the reactor performs a pretreatment with a biomass in an acidic medium.

A further subject of the invention is a method for treating lignocellulosic biomass comprising the following steps: —preparing an impregnation liquor containing a catalyst, in particular an acidic catalyst, —introducing the biomass into an impregnation reactor for impregnation with the impregnation liquor, —transferring the impregnated biomass to a pretreatment reactor for pretreatment therein by cooking, —enzymatically hydrolyzing the pretreated biomass, —alcoholically fermenting the enzymatic hydrolysis must obtained, wherein the method is carried out continuously over all or part of said steps, and wherein it pauses at the stage of pretreatment in the pretreatment reactor for the pretreatment reactor to be cleaned with the method as described above.

The biomass treatment method in question pauses for the pretreatment reactor to be cleaned, preferably according to a given frequency and/or on exceedance of a threshold value by a physicochemical or rheological characteristic of the reaction mixture in the reactor, measured or evaluated directly or indirectly. This may be, for example, a power threshold of the motor used to turn a conveying screw in the reactor, to turn stirring means in the reactor or any other moving component therein. For example, cleaning may be triggered when the torque of the conveying screw or of one of the conveying screws internal to the reactor increases by more than 15% relative to the torque observed at the start of production. It may also be triggered after a given period, which may range from 2 hours to 4 months of production.

A further subject of the invention is any plant for implementing the cleaning method according to the invention, which comprises a reactor for pretreating lignocellulosic biomass, a tank for preparing a basic aqueous solution, which is in fluid connection with said reactor for bringing the basic solution from the tank into the reactor and for recycling all or part of the basic solution, withdrawn from the reactor when it is drained, from the reactor to said tank, with means, optionally, for filtering the solution withdrawn from the reactor before it is reintroduced into the preparation tank. The proposed implementation of the invention therefore adds to the existing plant a tank for preparing the basic solution, which may be fed with water, with concentrated base (KOH or NaOH, for example, or any other organic or inorganic base), and optionally with basic solution recycled after draining of the reactor. This tank is equipped with known means for, in particular, keeping the pH of the solution constant, by adding KOH or water. The tank may also be equipped with heating means for bringing/maintaining the basic solution to/at the required temperature before introduction into the reactor. The heating means may alternatively or cumulatively be provided on the conduit-type fluidic connection means taking the basic solution from the tank to the reactor.

A further subject of the invention is any plant for implementing the abovementioned biomass treatment method wherein this plant comprises in succession a reactor for impregnating the biomass, fed with impregnating solution by a tank for preparing said solution, a reactor for pretreating the impregnated biomass, which is fed with basic aqueous solution by a tank for preparing said solution, an enzymatic hydrolysis reactor, and an alcoholic fermentation reactor, with all of the reactors being mounted in series, or at least two of them.

The enzymatic hydrolysis reactor may be the same as the alcoholic fermentation reactor, in the case of an SSCF (the acronym corresponds to the phrase "Simultaneous Saccharification and Co-Fermentation").

A further subject of the invention is also the biomass treatment method or plant described above for the treatment of biomass such as wood, straw, agricultural residues, and all dedicated energy crops, particularly annual or perennial plants such as miscanthus, in order to produce sugars, biofuels or biobased molecules.

DESCRIPTION OF THE EMBODIMENTS

The figures are highly schematic, with the same references corresponding to the same components from one figure to another. The equipment is shown substantially in the spatial position it occupies in the operational position.

The method for cleaning a biomass pretreatment reactor is illustrated here in the context of a biomass pretreatment method intended for producing alcohols, especially biofuel in the form of bioethanol, by the steps of the method according to FIG. 1, described rapidly below. One embodiment of this method is described in greater detail, for example, in patent WO 2018/015227, to which reference may be made as and when required.

It should be noted that the cleaning method according to the invention is equally applicable to any biomass treatment reactor, in particular but not solely for pretreatment, and, more generally, to any reactor intended for treatment of a lignocellulosic biomass, the purpose of the treatment being to modify a chemical, physical or rheological characteristic thereof, and being generally performed at elevated temperature.

Figure 1:
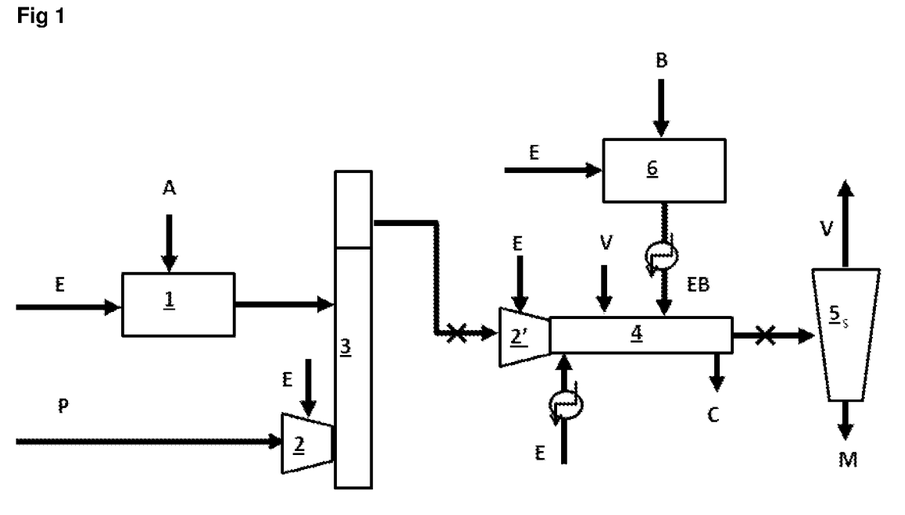
FIG. 1 represents the block diagram of the method for cleaning a biomass pretreatment reactor integrated into a biomass treatment method.

The biomass treatment method taken here as an example and represented in FIG. 1 comprises a first step of impregnating the biomass in a vertical reactor 3, followed by a step of pretreating the impregnated biomass in a steam explosion reactor 4. These steps of the method are carried out continuously and are detailed below with the aid of the description of the equipment used for its implementation:

A tank 1 is provided for preparing an impregnating liquor containing a chemical catalyst, which is made up from water E and catalyst A which are fed to the tank, the catalyst in the present instance being a strong acid such as concentrated sulfuric acid in aqueous phase, and this tank allowing the impregnation reactor 3 to be fed with a mixture of water E and chemical catalyst A, A conical screw 2 (also referred to as a "plug screw" or "sealing screw") for feeding fresh biomass (in this case the wheat straw P) into the impregnation reactor 3, An impregnation liquor feed for the reactor, connecting the liquor preparation tank 1 and the impregnation reactor 3, An impregnation reactor 3 equipped with two ascending transport screws (not shown) allowing the biomass to transit from the impregnation zone in the lower part of the reactor to the straining zone in the upper part of the reactor, and to take the impregnated and strained biomass at the reactor outlet at the top of the reactor. This impregnated and strained biomass is then sent for pretreatment via a feed opening out into a second conical screw 2'.

This second conical screw 2' feeds impregnated biomass to the pretreatment reactor 4, A pretreatment reactor 4 treats the impregnated biomass by steam explosion A water circuit is provided for washing the conical screws 2,2' of the impregnation reactor 3 and the pretreatment reactor 4, which are represented symbolically in FIG. 1 by inlets for water E at said screws A steam separation means 5 is fed by the reactor 4 with biomass which has undergone steam explosion cooking, as for example a cyclone separation means, with steam V at the top outlet and the exploded biomass, also called must M, at the bottom outlet.

At this stage this must M has sufficient accessibility of the cellulose to enzymes in order to be treated by enzymatic hydrolysis for the production of 2G sugars. The conditions of the enzymatic hydrolysis and of the consecutive or simultaneous fermentation which follow this separation (not shown in FIG. 1) are suitable for the desired products and are known to those skilled in the art.

The use of the above-described pretreatment technique results in the deposition of different types of biomass (wheat straw here, but also miscanthus, poplar, etc.), which build up/adhere to the surface of at least one of the transport screws internal to the pretreatment reactor 4, and to the walls of the pretreatment reactor 4. These deposits are subject to cooking for longer times than the normal residence time of the biomass in the reactor, and are converted into a residue, which here may also be called "coke". This "coke" can cause a variety of operational problems, such as plugging of the outlet orifice of the reactor 4, an increase in friction events on at least one of the internal transport screws on the wall of the chamber housing them, and a possible result of this is a reduction in performance of the pretreatment unit as a whole, as represented in FIG. 1.

Defining the composition of the "coke" has proven intricate, it being a residue with an appearance and composition evolving progressively over time: at the start of a production cycle, the material deposited is biomass, and so has essentially the same characteristics as the biomass which continues its way through the reactor 4 and toward the downstream steps. The deposit formed by adhesion on the inside wall of the reactor 4 will remain a much longer time than desired under the cooking conditions (temperature especially). The effect of the temperature affects the composition and morphology of the residue, which will become more and more a "baked" residue. The greater the extent to which the residue is "baked", the more compact it is and the more it sticks to the walls of the reactor.

These "coke" deposits are cumulative: the longer the tool is continuously operated, the greater the deposition of the coke, and the more the "layers" of coke close to the wall will turn into a very hard solid. These deposits therefore provoke a fouling phenomenon, increasing the thickness of the walls and reducing the useful volume of the reactor. Depending on the configuration of the cooking reactor, and in particular the type of internals in place, certain elements may be seen to have their rotation affected, such as the screw, or at least the screws transporting the biomass in the reactor in the course of cooking. This effect is manifested in particular in a rise in the power of the motor driving the relevant screw in rotation.

Throughout production, another possibility is for a more or less hardened section of this residue to break off from the wall of the reactor, under the effect, for example, of the rotation of the screw or at least one of the screws in question, or of the passage of the biomass through the reactor: accordingly, particles with a density much greater than the bed of biomass undergoing cooking may be caused to detach themselves and be carried toward the outlet orifice of the reactor, and this may give rise to instances of plugging or operational problems downstream. Despite these detachments, the deposits are found to continue increasing over time during a given production cycle.

After stoppage, cooling and opening of the cooking reactor 4, it was found that the coke takes two forms: a hard form in direct contact with the inside walls of the reactor, and a more friable form covering the hard coke. The difference between these two cokes lies in their elemental compositions, as indicated in table 1 below:

|  | Friable coke | Hard coke |
| --- | --- | --- |
| Carbon content (%) | 44.57 | 65.07 |
| Hydrogen content (%) | 5.85 | 4.67 |
| Oxygen content (%) | 34.63 | 24.58 |

It is found that the percentage of carbon in the hard coke is higher than that in the friable coke, while the opposite tendency is recorded for the oxygen content, and similar values for the hydrogen content. The conclusion is that the friable coke is in some way the precursor of the dense coke.

The invention involves halting the operation of the impregnation reactor 3 and pretreatment reactor 4, so as to carry out the chemical cleaning of the reactor 4 to extract this coke C. While this cleaning is a discontinuous step, it does not require opening of the reactor and mechanical cleaning of the reactor interior as was the case before. This cleaning according to the invention, detailed later on below, is therefore quicker, more economical and safer, as it limits the operational risks associated with the assembly and disassembly of the unit.

A working example of the method according to the invention and its variants are explained using the collective figures. It requires the following ancillary equipment, further to that already described, on the basis of FIG. 1:

A tank 6 for preparing a cleaning liquor EB containing a base. This tank 6 can be used to feed the pretreatment reactor 4 with basic solution at a certain concentration. It is fed with water E and with base B (for example from a base B in the form of a concentrated aqueous solution of KOH), the make-up of which is adjusted to give a liquor at the desired concentration of base and the desired pH. The concentration range of this basic solution is between 1 to 50 weight % of KOH and the pH of the solution is preferably greater than 8, preferably greater than 9 or 10, advantageously between 12 and 13. For example, the concentration may be 3 weight % KOH and the pH approximately 13.5 (a pH which will lower slightly when the solution has been introduced into the reactor, during the cleaning time).

A cleaning liquor feed to the reactor 4, connecting the cleaning liquor preparation tank 6 and the pretreatment reactor 4 for cleaning, by preheating it where appropriate with ad hoc equipment (resistance heaters surrounding the conduits, for example).

Figure 2:
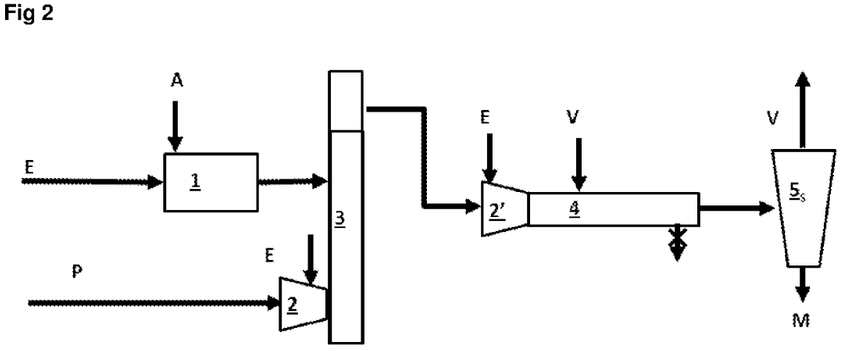
FIG. 2 represents a first phase of the cleaning method according to FIG. 1.

The exemplary embodiment of the method according to the invention runs as follows:

Sequence 1: Halt to production, as represented in FIG. 1 and in FIG. 3, with closure of the feed and the outlet of the pretreatment reactor 4 (shutoffs symbolized by a cross on the inlet and outlet conduits of the reactor), after which the reactor is drained, essentially drained of the biomass (FIG. 2 represents the biomass treatment method in production, before production is halted)

Figure 3:
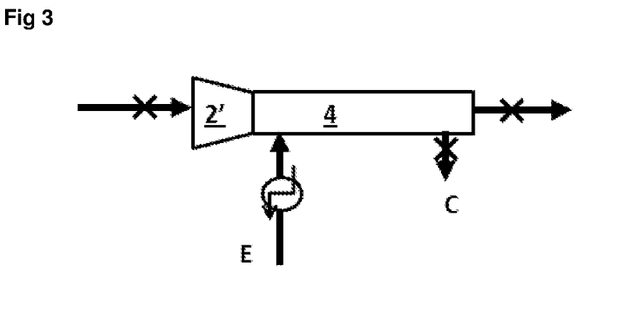
FIG. 3 represents a second phase of the cleaning method according to FIG. 1.

Sequence 2: Water bath by injection of water E heated to a certain temperature into the reactor 4, as shown in FIG. 3. The purpose of this first bath is to increase the pH of the residual biomass in the reactor so as to make the basic cleaning with the KOH solution more effective. The operating conditions are as follows: bath duration between 0 and 20 minutes, preferably less than or equal to 30 seconds; degree of filling of the reactor between 20 and 100% of its useful internal volume, for example 100%; the temperature of the preheated water before injection is between 20° C. (ambient temperature) to 90° C. (preheating), the water being preheated for example to a temperature of 80° C.

Figure 4:
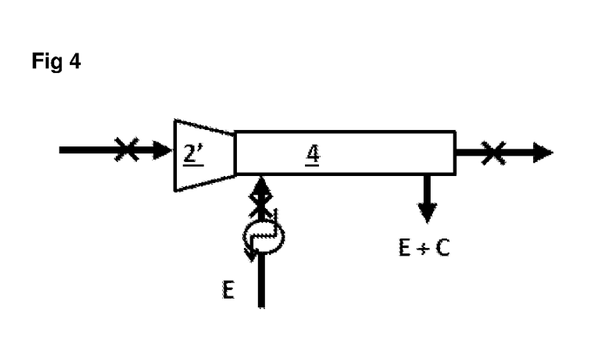
FIG. 4 represents a third phase of the cleaning method according to FIG. 1.
Figure 5:
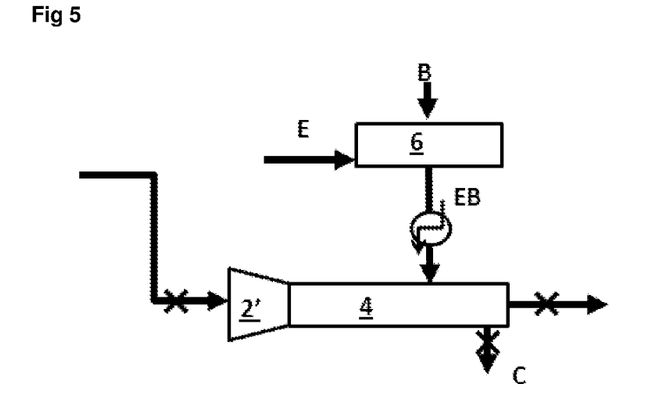
FIG. 5 represents a fourth phase of the cleaning method according to FIG. 1.

Sequence 3: Draining of the water contained in the reactor 4, as shown in FIG. 4 (the water E evacuated from the reactor is liable to contain coke, hence the indication E+C in the figure), Sequence 4: Filling of the reactor 4 with the basic solution EB, optionally preheated before being introduced into the reactor, from the preparation tank 6 for a certain duration, as shown in FIG. 5; the operating conditions are as follows: duration of reactor immersion between 30 seconds and 4 days, for example 2 hours; degree of filling of the reactor between 20 and 100% of its useful internal volume, for example 100%; the temperature of the basic solution before injection is between 20° C. (ambient temperature) and 90° C., the solution being preheated for example to a temperature of 80° C.

Figure 6:
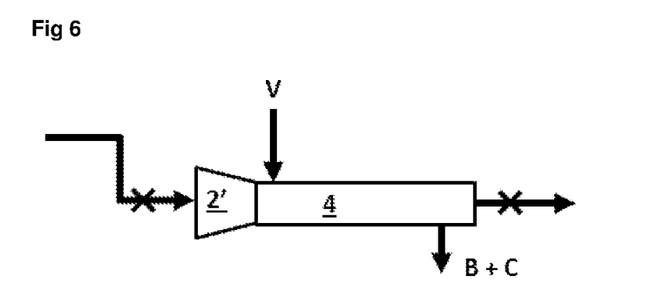
FIG. 6 represents a fifth phase of the cleaning method according to FIG. 1.
Figure 7:
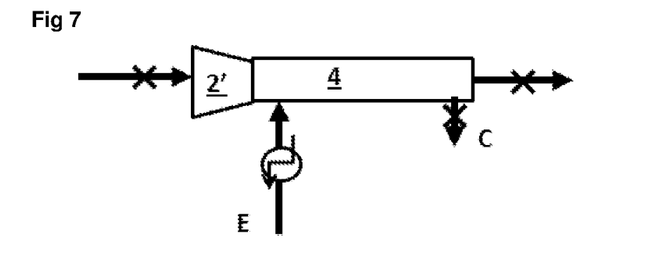
FIG. 7 represents a sixth phase of the cleaning method according to FIG. 1.

Sequence 5: Draining of the basic solution EB containing coke C, EB+C, from the reactor 4, as shown in FIG. 6, Sequence 6: Heating of the reactor 4 by injection of steam V, as also shown in FIG. 6. The objective here is to detach the pieces of biomass residue C by a thermal action complementary to that of the basic solution. The operating conditions are as follows: pressure between 1 and 20 bar ($1.10^5$ to $20.10^5$ Pa), for example 15 bar ($15.10^5$ Pa), the duration at constant steam-heating temperature is between 30 seconds and 6 hours, being for example 2 hours, Sequence 7: Water bath by injection of water E heated to a certain temperature into the reactor 4, as shown in FIG. 7. The operating conditions are as follows: bath duration from 0 to 20 minutes, for example at most 30 seconds; degree of filling of the reactor between 20 and 100% of its useful internal volume, for example 100%; the temperature of the preheated water before injection is between 20° C. (ambient temperature) to 90° C. (preheating), the water being preheated for example to a temperature of 80° C.

Figure 8:
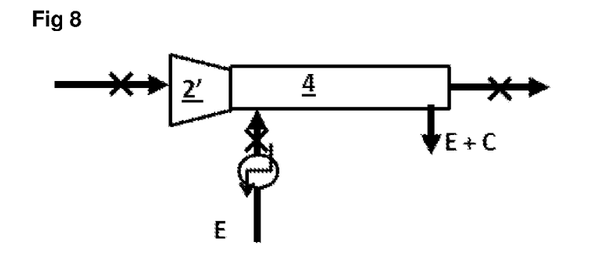
FIG. 8 represents a seventh phase of the cleaning method according to FIG. 1.

Sequence 8: Draining of the water E contained in the reactor 4, as shown in FIG. 8, then draining of the water E, optionally containing coke: E+C Sequences 9 and 10: A repetition of sequences 7 and 8 under the same operating conditions, i.e., a water bath by injection of water E heated to a certain temperature into the reactor, then draining of the water E, optionally containing coke: E+C, which may be followed by at least one further repetition of sequences 7 and 8.

The frequency of the cleaning procedure may vary widely depending on the type and size of the pretreatment reactor 4 and/or on the type of biomass treated. For example, cleaning may be triggered when the torque of one of the conveying screws of the reactor increases by more than 15% relative to the torque observed at the start of production.

A variety of variants may be provided to the exemplary cleaning method described above, while remaining within the ambit of the invention, and some of them are detailed below (they may be alternative or cumulative):

The aqueous solutions E and the basic solution EB may be introduced into the reactor 4 at the ambient temperature, or may be preheated, to 60, 80 and even 90° C. It should be noted that, even if introduced at ambient, they will generally tend to heat up when in the reactor, as the latter has a certain thermal inertia (since production of pretreated biomass takes place at high temperatures).

Figure 9:
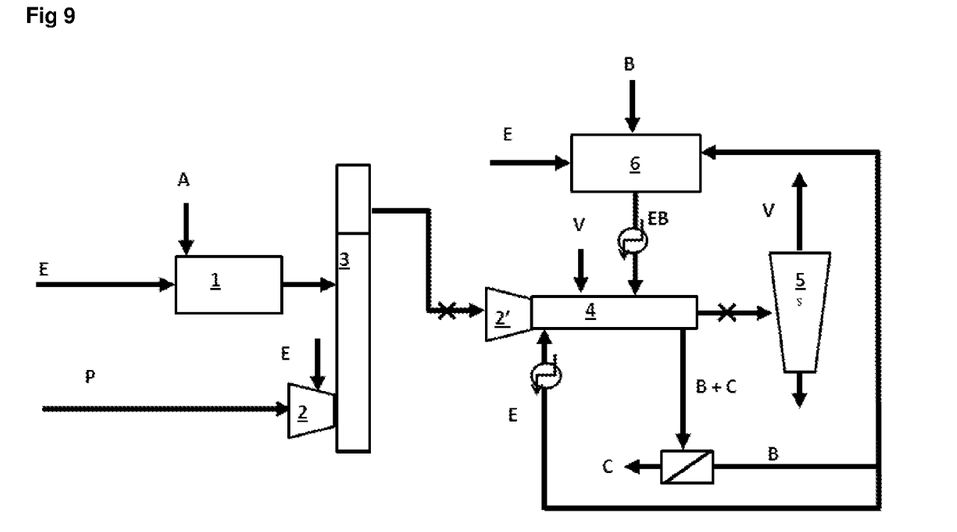
FIG. 9 represents a first way of recycling the basic solution used in the cleaning method according to FIG. 1.
Figure 10:
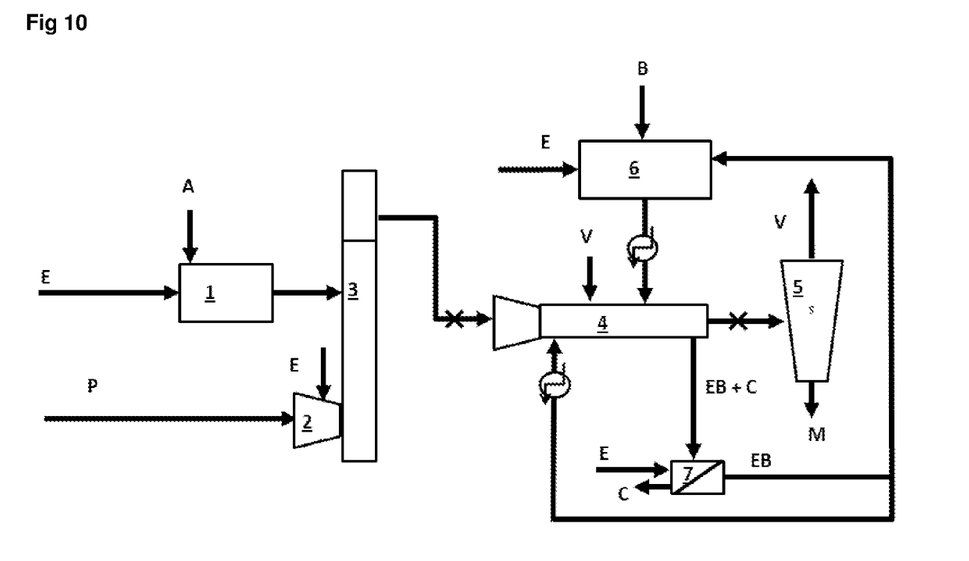
FIG. 10 represents a second way of recycling the basic solution used in the cleaning method according to FIG. 1.

The water bath sequences 2 and 3 before introduction of the basic liquor EB are optional and may therefore be omitted, The basic liquor B exiting the reactor 4 contains residues of degraded biomass, the "coke" described above: EB+C. This liquor may be filtered to extract its coke C, and then recycled either to the basic liquor preparation tank 6 or to carry out sequence 2 (water bath) of the cleaning procedure, as shown in FIG. 9, The coke C exiting the reactor 4 has a high base content. It may be washed with water E to extract its residual base, and then the washing water may be recycled either to the basic liquor preparation tank 6 or to carry out sequence 2 (water bath) of the cleaning procedure, as shown in FIG. 10. This is therefore a more extensive recycling than that proposed in FIG. 9.

Figure 11:
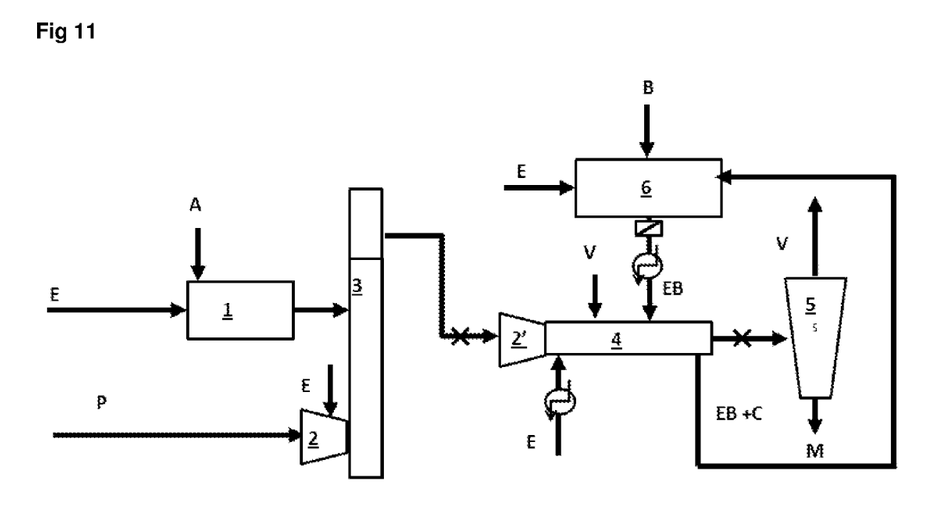
FIG. 11 represents a third way of recycling the basic solution used in the cleaning method according to FIG. 1.

The coke and also the basic liquor B+C exiting the reactor 4 may be sent directly into the basic liquor preparation tank 6, as shown in FIG. 11. The advantage is still to recover the residual base exiting the pretreatment reactor 4, as in the case of FIGS. 9 and 10, for preparing the basic liquor used to clean the reactor by immersion and to reduce the consumption of KOH. A filtration is then necessary before the basic solution B is injected into the pretreatment reactor 4.

The cleaning procedure may be applied in the case of a raw biomass treatment without a prior impregnation step (referred to then as autohydrolysis)

The interior volume of the reactor 4 may be immersed in the basic solution/liquor EB in the presence of a solid abrasive compatible with the mechanical operation of the reactor, to produce an auxiliary mechanical effect to the detachment of the coke from the walls of the reactor. The particles may be introduced into the reactor 4 either separately or in the basic liquor B.

Throughout the present text, the abbreviation "SC" denotes the solids content, which is measured according to the standard ASTM E1756-08(2015) "Standard Test Method for Determination of Total Solids in Biomass".

EXAMPLES

Example 1: Not in Accordance with the Invention

This example was carried out with wheat straw as biomass. The characteristics and composition of the feedstock are as follows:

Solids content (SC): 91.07%
Biomass flow rate: 65 kg SC/h

The operating conditions for producing the pretreated biomass are as follows:

Impregnation for production and cleaning in the impregnation reactor 3:
$H_2SO_4$ acidic solution flow rate: 1.5 kg/h (pH close to 1)
Steam explosion of the impregnated biomass in the pretreatment reactor 4:
Residence time: 5 min
Duration of production: 72 hours
Prior-art mechanical cleaning:
Temperature decrease: 48 hours
Duration of opening and disassembly: 8 hours
Duration of cleaning: 8 hours
Duration of reassembly: 8 hours The mass of coke C produced is 16 kg, occupying a volume of 0.012 m³ in the reactor 4, giving a reduction in reactor volume of 8.7% and a coke production rate of 222 g/h.

Example 2: in Accordance with the Invention

The impregnation and steam explosion are performed under the same conditions and with the same biomass as in example 1.

The halt in production is followed immediately by cleaning of the reactor 4 in accordance with the invention, under the following conditions:

Water bath at 80° C. with a degree of filling of 100%, then immediate draining of the reactor,
Immersion of the entirety of the useful internal volume (corresponding to a degree of filling of 100%) of the reactor 4 in the basic solution B containing 3% of KOH, corresponding to an initial pH before injection into the reactor of 13.6. Before being injected, the basic solution was heated at 80° C. for 2 hours. The reactor 4 is then drained,
Heating of the reactor 4 for 2 hours at 200° C. (no biomass present), by steam injection,
3 rinses with hot water at 80° C. with complete immersion of the internal volume of the reactor 4 (degree of filling: 100%), then immediate draining The mass of coke recovered at the end of the cleaning procedure is 15 kg, giving a coke production rate of 208 g/h. The cleaning procedure thus allowed recovery of 94% of the coke formed in the reactor 4, so reducing its fouling rate by 94%.

The time needed for carrying out this chemical cleaning is markedly less than the time needed for the mechanical cleaning of comparative example 1. The cleaning method of the invention is also much less intrusive, as it does not require the reactor to be opened.

The invention claimed is:

1. A method for cleaning a reactor (4) for treating a lignocellulosic biomass (P), said method comprising the following sequence of steps:
   a) draining the reactor of the reaction mixture containing the biomass,
   b) filling the reactor with a basic aqueous solution (EB),
   c) draining the reactor,
   d) injecting steam (V) into the reactor,
   e) filling the reactor with an aqueous solution (E),
   f) draining the reactor, and
      wherein, during draining step c), the basic solution drained is recovered for recycling, with optional filtration to remove solid residues (C).

2. The method as claimed in claim 1, wherein it comprises at least one step a') of filling the reactor (4) with an aqueous solution (E), followed by a step a") of draining the reactor, between step a) of draining the reaction mixture and step b) of filling with a basic aqueous solution (EB).

3. The method as claimed in claim 1, wherein it further comprises, after step a), introducing particles of solid abrasive material into the reactor (4), either separately or by introducing the particles into the basic solution (EB) or into the or one of the aqueous solution(s) (E).

4. The method as claimed in claim 1, wherein the basic aqueous solution (EB) and/or the or one of the aqueous solution(s) (E) is or are heated before introduction into the reactor (4), to a temperature of at least 20° C., and at most 90° C.

5. The method as claimed in claim 1, wherein at least step b) of filling the reactor (4) with the basic aqueous solution (EB) takes place with the interior volume of the reactor at a temperature of at least 60° C.

6. The method as claimed in claim 1, wherein, during draining step c), the basic solution drained is filtered for recovery of the solid residues (C) it contains, and in that these residues are treated for extraction of the basic solution from them for recycling thereof.

7. The method as claimed in claim 1, wherein the immersion of the reactor (4) with the basic solution (EB), when the reactor has been filled as per step b), before it is drained, has a duration of between 30 seconds and 4 days.

8. The method as claimed in claim 1, wherein the degree of filling of the reactor (4) with the biomass (EB) and/or with the or one of the aqueous solution(s) (E) is between 20 and 100%.

9. The method as claimed in claim 1, wherein the steam (V) in step d) is injected at a pressure of between $1.10^5$ and $20.10^5$ Pa.

10. The method as claimed in claim 1, wherein steps e) and f) are repeated at least twice.

11. A method for treating lignocellulosic biomass (P), comprising:

preparing an impregnation liquor containing a catalyst, in particular an acidic catalyst, —introducing the biomass into an impregnation reactor (3) for impregnation with the impregnation liquor, transferring the impregnated biomass to a pretreatment reactor (4) for pretreatment therein by cooking, enzymatically hydrolyzing the pretreated biomass, alcoholically fermenting the enzymatic hydrolysis must obtained, wherein the method is carried out continuously over all or part of said steps, and in that it pauses at the stage of pretreatment in the pretreatment reactor for the pretreatment reactor to be cleaned with the method as claimed in claim 1.

12. The method as claimed in claim 1, wherein it pauses for the pretreatment reactor (4) to be cleaned according to a given frequency and/or on exceedance of a threshold value by a physicochemical or rheological characteristic of the reaction mixture in the reactor.

13. A plant for implementing the method as claimed in claim 1, wherein it comprises a reactor (4) for pretreating lignocellulosic biomass, a tank (6) for preparing a basic aqueous solution (EB), which is in fluid connection with said reactor for bringing the basic solution (EB) from the tank into the reactor and for recycling all or part of the basic solution, withdrawn from the reactor when it is drained, from the reactor to said tank, with means, optionally, for filtering the solution withdrawn from the reactor before it is reintroduced into the preparation tank.

14. A plant for implementing the method as claimed in claim 11, wherein it comprises in succession a reactor (3) for impregnating the biomass (P), fed with impregnating solution by a tank (1) for preparing said solution, a reactor (4) for pretreating the impregnated biomass, which is fed with basic aqueous solution (EB) by a tank (6) for preparing said solution, an enzymatic hydrolysis reactor, and an alcoholic fermentation reactor, with all of the reactors being mounted in series, or at least two of them.

* * * * *